(12) United States Patent
Berisha et al.

(10) Patent No.: US 12,175,998 B2
(45) Date of Patent: Dec. 24, 2024

(54) SPEECH ANALYSIS DEVICES AND METHODS FOR IDENTIFYING MIGRAINE ATTACKS

(71) Applicants: Arizona Board of Regents on behalf of Arizona State University, Scottsdale, AZ (US); Mayo Foundation for Medical Education and Research, Rochester, MN (US)

(72) Inventors: Visar Berisha, Tempe, AZ (US); Jacob Peplinski, Gilbert, AZ (US); Todd Schwedt, Phoenix, AZ (US)

(73) Assignees: Arizona Board of Regents on behalf of Arizona State University, Tempe, AZ (US); Mayo Foundation for Medical Education and Research, Rochester, MN (US)

( * ) Notice: Subject to any disclaimer, the term of this patent is extended or adjusted under 35 U.S.C. 154(b) by 502 days.

(21) Appl. No.: 17/292,339

(22) PCT Filed: Nov. 8, 2019

(86) PCT No.: PCT/US2019/060386
§ 371 (c)(1),
(2) Date: May 7, 2021

(87) PCT Pub. No.: WO2020/097412
PCT Pub. Date: May 14, 2020

(65) Prior Publication Data
US 2022/0005494 A1    Jan. 6, 2022

Related U.S. Application Data

(60) Provisional application No. 62/758,511, filed on Nov. 9, 2018.

(51) Int. Cl.
*G10L 25/66* (2013.01)
*A61B 5/00* (2006.01)
*G10L 25/72* (2013.01)

(52) U.S. Cl.
CPC ............ *G10L 25/66* (2013.01); *A61B 5/4803* (2013.01); *A61B 5/4824* (2013.01);
(Continued)

(58) Field of Classification Search
CPC ......... G10L 25/66; G10L 25/72; G10L 25/48; G10L 25/51; A61B 5/4803; A61B 5/4824;
(Continued)

(56) References Cited

U.S. PATENT DOCUMENTS

2016/0360970 A1* 12/2016 Tzvieli ................. A61B 5/0075
2018/0000425 A1*  1/2018 Hernacki .............. A61B 5/746
2019/0221228 A1*  7/2019 Meshram .............. G16H 70/60

OTHER PUBLICATIONS

Jensen K, Tfelt-Hansen P, Lauritzen M, Olesen J. Classic migraine. A prospective recording of symptoms. Acta Neural Scand 1986; 73:359-362. (Year: 1986).*

(Continued)

*Primary Examiner* — Bhavesh M Mehta
*Assistant Examiner* — Darioush Agahi
(74) *Attorney, Agent, or Firm* — Polsinelli PC

(57) ABSTRACT

Speech analysis devices and methods for identifying migraine attacks are provided. Migraine sufferers can experience changes in speech patterns both during a migraine attack and in a pre-attack phase (e.g., a time period before the migraine attack can be recognized by the migraine sufferer). Embodiments identify or predict migraine attacks during the pre-attack phase and/or the attack phase (such as early stages of a migraine attack) by comparing speech features from one or more speech samples provided by a user against baseline data. The speech features are indicative (Continued)

and/or predictive of migraine onset, and can be personalized to a user and/or based on normative data.

21 Claims, 12 Drawing Sheets

(52) U.S. Cl.
CPC .......... *A61B 5/7267* (2013.01); *A61B 5/7282* (2013.01); *A61B 5/742* (2013.01); *G10L 25/72* (2013.01)

(58) Field of Classification Search
CPC ..... A61B 5/7267; A61B 5/7282; A61B 5/742; A61B 5/4076; A61B 5/02055; A61B 5/7405; A61B 2560/0242; A61B 5/7264
See application file for complete search history.

(56) References Cited

OTHER PUBLICATIONS

Sandoval S, Berisha V, Utianski RL, Liss JM, Spanias A Automatic assessment of vowel space area. J Acoust Soc Am 2013;134: EL477-EL483. (Year: 2013).*
Quintela E et. al. Premonitory and resolution symptoms in migraine: a prospective study in 100 unselected patients. Cephalalgia 2006;26: 1051-1060. (Year: 2006).*
Petrusic I, Zidverc-Trajkovic J, Podgorac A, Sternic N. Underestimated phenomena: higher cortical dysfunctions during migraine aura. Cephalalgia 2013;33:861-867. (Year: 2013).*
Petrusic I, Pavlovski V, Vucinic D, Jancic J. Features of migraine aura in teenagers. J Headache Pain 2014; 15:87. (Year: 2014).*
Jiao Y, Berisha V, Liss J, Hsu SC, Levy E, McAuliffe M. Articulation entropy: An unsupervised measure of articulatory precision. IEEE Signal Processing Letters 2016;24:485-489 (Year: 2016).*
Jiao Y, Berisha V, Tu M, Liss J. Convex weighting criteria for speaking rate estimation. IEEE/ACM Tans Audio Speech Lang Process 2015;23:1421-1430. (Year: 2016).*
Classification Committee of the International Headache Society. The International Classification of Headache Disorders-3 beta. Cephalalgia 2013; 33:629-808. (Year: 2013).*
Haley et al., Foreign accent syndrome due to conversion disorder: Phonetic analyses and clinical course, Journal of Neurolinguistincs, Pergamon, Amsterdam, NL, vol. 23, No. 1, Jan. 1, 2010, pp. 28-43, XP026700405, ISSN: 0911-6044, DOI: 10.1016/J.JNeuroling.2009. 08.001. (Year: 2010).*
Giffin NJ et al. Premonitory symptoms in migraine: an electronic diary study. Neurology 2003; 60:935-940. (Year: 2003).*
Crisp AH, Levett G, Davies P, et al. Cerebral hemisphere function and migraine. J Psychiat Res 1989; 23:201-212. (Year: 1989).*
Sjaastad 0, Bakketeig LS, Petersen HC. Migraine with aura: visual disturbances and interrelationship with the pain phase. Vaga study of headache epidemiology. J Headache Pain 2006;7: 127-135. (Year: 2006).*
Schwedt, Todd J,. Peplinski, J., Pamela Gracia-Fillion, P. and Berisha, V., "Altered speech with migraine attackes: A prospective, longitudinal study of episodic migraine without aura," Cephalalgia, 2019, vol. 39(6), 2019, pp. 722-731. (Year: 2019).*
Berisha V. Sandoval S, Utianski R, Liss J, Spanias A Characterizing the distribution of the quadrilateral vowel space area. The Journal of the Acoustical Society of America 2014; 135:421-427. (Year: 2014).*
Jensen K, Tfelt-Hansen P, Lauritzen M, Olesen J. Classic migraine. A prospective recording of symptoms. Acta Neurol Scand 1986;73:359-362.
Sandoval S, Berisha V, Utianski RL, Liss JM, Spanias A. Automatic assessment of vowel space area. J Acoust Soc Am 2013; 134: EL477-EL483.
Quintela E et. al. Premonitory and resolution symptoms in migraine: a prospective study in 100 unselected patients. Cephalalgia 2006;26:1051-1060.
Petrusic I, Zidverc-Trajkovic J, Podgorac A, Sternic N. Underestimated phenomena: higher cortical dysfunctions during migraine aura. Cephalalgia 2013;33:861-867.
Petrusic I, Pavlovski V, Vucinic D, Jancic J. Features of migraine aura in teenagers. J Headache Pain 2014; 15:87.
Jiao Y, Berisha V, Liss J, Hsu SC, Levy E, McAuliffe M. Articulation entropy: An unsupervised measure of articulatory precision. IEEE Signal Processing Letters 2016;24:485-489.
Jiao Y, Berisha V, Tu M, Liss J. Convex weighting criteria for speaking rate estimation. IEEE/ACM Tans Audio Speech Lang Process 2015;23:1421-1430.
Classification Committee of the International Headache Society. The International Classification of Headache Disorders-3 beta. Cephalalgia 2013;33:629-808.
Haley et al., Foreign accent syndrome due to conversion disorder: Phonetic analyses and clinical course, Journal of Neurolinguistincs, Pergamon, Amsterdam, NL, vol. 23, No. 1, Jan. 1, 2010, pp. 28-43, XP026700405, ISSN: 0911-6044, DOI: 10.1016/J.JNeuroling.2009. 08.001.
Giffin NJ et al. Premonitory symptoms in migraine: an electronic diary study. Neurology 2003;60:935-940.
Crisp AH, Levett G, Davies P, et al. Cerebral hemisphere function and migraine. J Psychiat Res 1989;23:201-212.
Sjaastad O, Bakketeig LS, Petersen HC. Migraine with aura: visual disturbances and interrelationship with the pain phase. Vaga study of headache epidemiology. J Headache Pain 2006;7:127-135.
Schwedt, Todd J,. Peplinski, J., Pamela Gracia-Fillion, P. and Berisha, V., "Altered speech with migraine attackes: A prospective, longitudinal study of episodic migraine without aura," Cephalalgia, 2019, vol. 39(6), 2019, pp. 722-731.
Berisha V. Sandoval S, Utianski R, Liss J, Spanias A. Characterizing the distribution of the quadrilateral vowel space area. The Journal of the Acoustical Society of America 2014; 135:421-427.

* cited by examiner

|  | Migraine (n=15) |
|---|---|
| Headache Frequency in days/month: baseline report (mean +/- SD) | 9.3 +/- 2.8 |
| Headache Frequency in days/month: per diary (mean +/- SD) | 8.9 +/- 4.1 |
| Migraine Attack Frequency per month: baseline report | 6.2 +/- 2.3 |
| Migraine Attack Frequency per month: per diary | 6.8 +/- 4.3 |
| % Patients Reporting Premonitory Symptoms | 100% |
| % Migraine attacks with premonitory symptoms reported at baseline (mean +/- SD) | 90 +/-14.9 |
| % Migraine attacks with premonitory symptoms per diary | 72.1% |

FIG. 1

|  | Premonitory Symptom Reported at Baseline (% of patients with symptom) | Premonitory Symptom Reported in Diary (% of patients with symptom) |
|---|---|---|
| Light Sensitivity | 67 | 73 |
| Neck Stiffness | 67 | 80 |
| Generalized Feeling of Being Unwell | 60 | 87 |
| Fatigue/Tiredness | 60 | 87 |
| Sound Sensitivity | 53 | 47 |
| Mood Change | 47 | 80 |
| Odor Sensitivity/ Distortions | 40 | 27 |
| Dizzy/ Lightheaded | 40 | 67 |
| Temperature Change (e.g. chills, sweats) | 40 | 67 |
| Yawning | 33 | 67 |
| Muscle Pain | 27 | 60 |
| Vision Change | 27 | 53 |
| Nausea | 27 | 67 |
| Problems Speaking | 20 | 27 |
| Facial Flushing/ Pale Face | 13 | 33 |
| Food Cravings | 13 | 40 |
| GI Symptoms | 7 | 33 |
| Increased Urination | 0 | 33 |

FIG. 2

| | Healthy Controls (mean/sd) | Interictal Phase (mean/sd) | Pre-Attack Phase (mean/sd) | Migraine Attack (mean/sd) |
|---|---|---|---|---|
| Speaking Rate [syllables/s] | 4.995/0.719 | 5.301/0.757 | 5.035/0.824 | 5.054/0.728 |
| Pause Rate [% of recording length] | 1.1/1.9 | 1.4/4.9 | 1.8/4.7 | 1.7/4.0 |
| Articulation Rate [syllables/s] | 5.049/0.697 | 5.413/1.510 | 5.144/0.894 | 5.149/0.745 |
| Articulation Entropy | 97.68/16.47 | 98.36/17.48 | 91.00/17.45 | 90.52/19.91 |
| Vowel Space Area [$Hz^2$] | 2.186E5/1.529E5 | 2.152E5/1.734E5 | 2.579E5/4.433E5 | 2.337E5/1.738E5 |
| Energy Decay Slope [dB/s] | -0.304/0.605 | -0.354/0.508 | -0.500/0.450 | -0.377/0.520 |
| Phonatory Duration [s] | 12.794/5.865 | 9.423/3.291 | 9.123/3.294 | 8.834/3.839 |
| Average Pitch [Hz] | 172.56/32.81 | 174.21/36.31 | 171.54/32.57 | 171.05/34.87 |

FIG. 3

|  | Comparisons within Migraine Group | | | Migraine vs. Healthy Control | | |
|---|---|---|---|---|---|---|
|  | Migraine Atack vs Interictal | Migraine Attack vs Pre-Attack | Interictal vs Pre-Attack | Migraine Attack vs Healthy Control | Interictal vs Healthy Control | Pre-Attack vs Healthy Control |
| Speaking Rate | 0.000 | 0.893 | 0.000 | 0.304 | 0.000 | 0.498 |
| Pause Rate | 0.281 | 0.617 | 0.539 | 0.044 | 0.143 | 0.030 |
| Articulation Rate | 0.000 | 0.932 | 0.000 | 0.086 | 0.000 | 0.134 |
| Articulation Entropy | 0.000 | 0.956 | 0.000 | 0.000 | 0.358 | 0.000 |
| Vowel Space Area | 0.296 | 0.475 | 0.421 | 0.379 | 0.698 | 0.192 |
| Energy Decay Slope | 0.570 | 0.778 | 0.439 | 0.083 | 0.040 | 0.000 |
| Phonatory Duration | 0.049 | 0.581 | 0.159 | 0.000 | 0.000 | 0.000 |
| Average Pitch | 0.576 | 0.835 | 0.315 | 0.108 | 0.408 | 0.730 |

FIG. 4

| Subject | 01 | 05 | 06 | 09 | 13 | 14 | 16 | 18 | 19 |
|---|---|---|---|---|---|---|---|---|---|
| Speaking Rate | 0.023 | 0.004 | 0.003 | 0.542 | 0.003 | 0.041 | 0.099 | 0.048 | 0.000 |
| Pause Rate | 0.909 | 0.321 | 0.416 | 0.126 | 0.501 | 0.041 | 0.212 | 0.926 | 0.078 |
| Articulation Rate | 0.089 | 0.001 | 0.002 | 0.359 | 0.039 | 0.022 | 0.113 | 0.027 | 0.000 |
| Articulation Entropy | 0.892 | 0.696 | 0.000 | 0.002 | 0.912 | 0.067 | 0.046 | 0.035 | 0.037 |
| Vowel Space Area | 0.550 | 0.464 | 0.002 | 0.018 | 0.749 | 0.690 | 0.783 | 0.373 | 0.292 |
| Energy Decay Slope | 0.087 | 0.027 | 0.062 | 0.810 | 0.663 | 0.155 | 0.987 | 0.298 | 0.055 |
| Phonatory Duration | 0.000 | 0.666 | 0.857 | 0.025 | 0.194 | 0.370 | 0.421 | 0.011 | 0.027 |
| Average Pitch | 0.705 | 0.120 | 0.020 | 0.134 | 0.333 | 0.986 | 0.192 | 0.003 | 0.001 |

*FIG. 5*

| Subject | 05 | 06 | 09 | 12 | 14 | 16 | 17 | 18 | 19 |
|---|---|---|---|---|---|---|---|---|---|
| Speaking Rate | 0.050 | 0.000 | 0.579 | 0.608 | 0.020 | 0.564 | 0.612 | 0.020 | 0.488 |
| Pause Rate | 0.130 | 0.132 | 0.293 | 0.158 | 0.377 | 0.063 | 0.797 | 0.366 | 0.402 |
| Articulation Rate | 0.332 | 0.000 | 0.398 | 0.226 | 0.046 | 0.664 | 0.594 | 0.007 | 0.644 |
| Articulation Entropy | 0.519 | 0.000 | 0.038 | 0.543 | 0.085 | 0.728 | 0.043 | 0.124 | 0.397 |
| Vowel Space Area | 0.752 | 0.192 | 0.005 | 0.672 | 0.023 | 0.449 | 0.749 | 0.012 | 0.528 |
| Energy Decay Slope | 0.239 | 0.161 | 0.343 | 0.031 | 0.240 | 0.038 | 0.080 | 0.288 | 0.000 |
| Phonatory Duration | 0.103 | 0.274 | 0.075 | 0.212 | 0.020 | 0.585 | 0.142 | 0.009 | 0.100 |
| Average Pitch | 0.120 | 0.000 | 0.411 | 0.102 | 0.137 | 0.399 | 0.699 | 0.200 | 0.835 |

FIG. 7

SPEECH ANALYSIS DEVICES AND METHODS FOR IDENTIFYING MIGRAINE ATTACKS

STATEMENT OF RELATED APPLICATION(S)

This application claims the benefit of U.S. Provisional Patent Application No. 62/758,511 filed on Nov. 9, 2018, the disclosure of which is hereby incorporated by reference herein in its entirety.

TECHNICAL FIELD

This application relates to audio processing of human speech.

BACKGROUND

Migraine is a disabling neurological condition manifesting with attacks of headache, hypersensitivities to visual, auditory, olfactory, and somatosensory stimuli, as well as nausea and vomiting. Migraine attacks are sometimes preceded by an aura, which is a neurological disturbance that can manifest in various ways. Auras frequently involve visual disturbances, but can also involve sensory, motor, and/or verbal disturbances. A visual aura includes visual disturbances that spread slowly across the visual field, often including positive symptoms (e.g., flashes) followed by negative symptoms (e.g., scotoma). A sensory aura frequently includes tingling that spreads on one side of a person's face and/or upper extremity. Another aura (known as dysphasic aura) causes transient speech or language problems. A migraine aura usually precedes a migraine attack, but can also occur during the attack, or can even occur without an associated headache.

Difficulties with speech and language have been documented during the aura phase of migraine. Although changes in speech during other phases of the migraine attack are reported by patients, objectively measured changes in speech associated with migraine have been inadequately investigated during the non-aura phases of the migraine attack.

Changes in speech patterns during migraine attacks might be expected given the relatively widespread alterations in brain function and functional connectivity that occur during migraine attacks. A person's ability to share thoughts and ideas through spoken communication is a complex and fragile process. Even the simplest verbal response requires a complex sequence of events. It requires thinking of the words that best convey the message, sequencing these words in an order that is allowed in the language, and then sending signals to the muscles required to produce speech. Even the slightest disturbance to the brain areas that orchestrate these events can manifest in speech problems.

Currently practiced abortive treatment of migraine attacks is reactive. A patient must wait for the patient's migraine symptoms to become obvious and then react with abortive measures, such as taking medication and avoiding exacerbating factors (e.g., exposure to light and noise, physical activity). In addition, lack of objective measures of migraine attacks as they occur can result in patients being unaware that a migraine has started, leading to delayed treatment. Delayed treatment is less effective than early treatment, thereby leading to needless suffering. Research has shown that early detection and early treatment of migraine attacks substantially improve outcomes.

SUMMARY

Speech analysis devices and methods for identifying migraine attacks are provided. Migraine sufferers can experience changes in speech patterns both during a migraine attack and in a pre-attack phase (e.g., a time period before the migraine attack can be recognized by the migraine sufferer). Embodiments identify or predict migraine attacks during the pre-attack phase and/or the attack phase (such as early stages of a migraine attack) by comparing speech features from one or more speech samples provided by a user against baseline data. The speech features are indicative and/or predictive of migraine onset, and can be personalized to a user and/or based on normative data.

In some examples, a speech sample is elicited from a user (e.g., periodically or on demand), and a multi-dimensional statistical signature of the user's current speech production abilities is generated for the speech sample (e.g., based on the speech features). The multi-dimensional statistical signature is compared against one or more baseline statistical signatures of speech production ability. The one or more baseline statistical signatures can be derived or obtained from the user in some examples, and can alternatively or additionally be based on normative data from a database (e.g., other users). This approach provides a tool to enable migraine sufferers to take therapeutic measures before a full-blown migraine occurs. Such therapeutic measures may avoid the migraine attack or reduce its severity, thereby reducing any disability associated with a migraine attack. In some cases, information derived from the speech sample(s) is also combined with additional data collected by sensors or input by the user, such as exposure to potential migraine triggers and self-reported symptoms that may occur during a premonitory phase of migraine. Such additional data may be part of the multi-dimensional statistical signature or may be used in analyzing the multi-dimensional statistical signature.

In an exemplary embodiment, a migraine identification device is provided. The migraine identification device includes audio input circuitry configured to provide an input signal that is indicative of speech provided by a user. The migraine identification device further includes signal processing circuitry configured to receive the input signal. The signal processing circuitry is further configured to process the input signal to generate an instantaneous multi-dimensional statistical signature of speech production abilities of the user, and compare the multi-dimensional statistical signature against one or more baseline statistical signatures of speech production ability derived or obtained from the user. The signal processing circuitry is further configured to provide a migraine identification signal based on the multi-dimensional statistical signature comparison. The migraine identification device further includes a notification element coupled to the signal processing circuitry, the notification element being configured to receive the migraine identification signal and provide at least one notification signal to the user.

In some examples, the multi-dimensional statistical signature spans one or more of the following perceptual dimensions: articulation, prosodic variability, phonation changes, rate, and rate variation.

In some examples, processing the input signal comprises measuring speech features represented in the input signal, the speech features comprising one or more of speaking rate, articulation rate, articulation entropy, vowel space area, energy decay slope, phonatory duration, and average pitch. In some examples, comparing the multi-dimensional statistical signature against the one or more baseline statistical signatures of speech production ability comprises comparing each speech feature to a corresponding baseline speech feature of the one or more baseline statistical signatures of speech production ability.

In some examples, processing the input signal is based on the input signal and additional data comprising one or more of sensor data, a time of day, an ambient light level, or a device usage pattern of the user. In some examples, processing the input signal further comprises selecting or adjusting the one or more baseline statistical signatures of speech production ability based on the additional data.

In some examples, the migraine identification device is a mobile computing device operating a migraine identification application. In some examples, the migraine identification application queries the user periodically to provide a speech sample from which the input signal is derived. In some examples, the migraine identification application facilitates the user spontaneously providing a speech sample from which the input signal is derived. In some examples, the migraine identification application passively detects changes in speech patterns of the user and initiates generation of the instantaneous multi-dimensional statistical signature of speech production abilities of the user.

In some examples, the notification element comprises a display. In some examples, the signal processing circuitry is further configured to cause the display to prompt the user to provide a speech sample from which the input signal is derived. In some examples, the at least one notification signal comprises a display notification instructing the user to take action to relieve migraine symptoms.

In another exemplary embodiment, a method for identifying a migraine is provided. The method includes receiving an input signal that is indicative of speech provided by a user. The method further includes extracting a multi-dimensional statistical signature of speech production abilities of the user from the input signal. The method further includes comparing the multi-dimensional statistical signature against one or more baseline statistical signatures of speech production ability. The method further includes providing a migraine identification signal based on the multi-dimensional statistical signature comparison.

In another exemplary embodiment, a non-transient computer readable medium is provided. When executed by a computer, the non-transient computer readable medium causes the computer to receive an input signal that is indicative of speech provided by a user. The non-transient computer readable medium further causes the computer to extract a multi-dimensional statistical signature of speech production abilities of the user from the input signal. The non-transient computer readable medium further causes the computer to compare the multi-dimensional statistical signature against one or more baseline statistical signatures of speech production ability. The non-transient computer readable medium further causes the computer to provide a migraine identification signal based on the multi-dimensional statistical signature comparison.

In another aspect, any one or more aspects or features described herein may be combined with any one or more other aspects or features for additional advantage.

Other aspects and embodiments will be apparent from the detailed description and accompanying drawings.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

FIG. 1 is a table providing reported values for migraine characteristics, including headache frequency, migraine attack frequency, percentage of patients reporting premonitory symptoms, and percentage of reported migraine attacks with premonitory symptoms.

FIG. 2 is a table providing premonitory symptoms reported at baseline and premonitory symptoms reported in diary (expressed in percentage of patients with a given symptom).

FIG. 3 is a table providing speech features for healthy controls and participants with migraine during interictal, pre-attack, and migraine attack phases.

FIG. 4 is a table providing p-values for comparison of eight speech features (speaking rate, pause rate, articulation rate, articulation entropy, vowel space area, energy decay slope, phonatory duration, and average pitch), including comparisons within a migraine group as well as comparisons of migraine versus healthy control groups.

FIG. 5 is a table providing p-values for eight speech features (speaking rate, pause rate, articulation rate, articulation entropy, vowel space area, energy decay slope, phonatory duration, and average pitch) for migraine attack versus interictal phase for nine individual participants.

FIG. 7 is a table providing p-values for eight speech features (speaking rate, pause rate, articulation rate, articulation entropy, vowel space area, energy decay slope, phonatory duration, and average pitch) for migraine pre-attack versus interictal phase for nine individual patients.

DETAILED DESCRIPTION

Figure 6A:
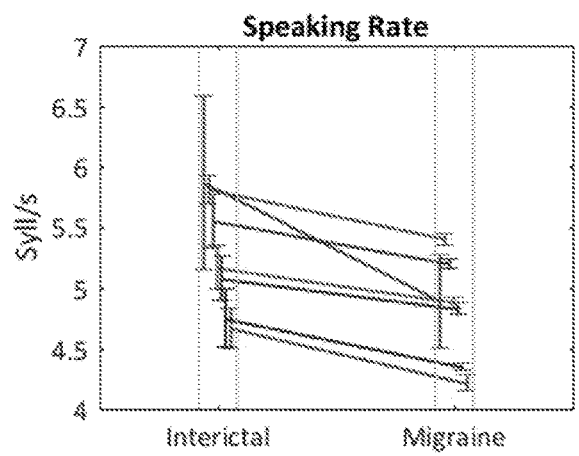
FIGS. 6A-6H are line charts providing mean and standard error plots for the eight speech features of FIG. 5 that significantly differed during interictal versus migraine attack phases, with each line representing a single individual participant with migraine.
Figure 6B:
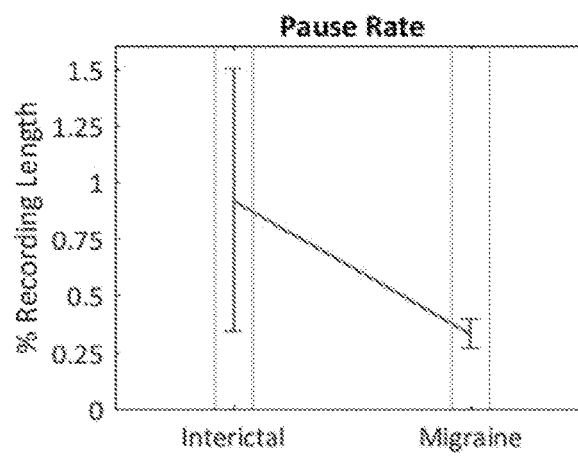
Figure 6C:
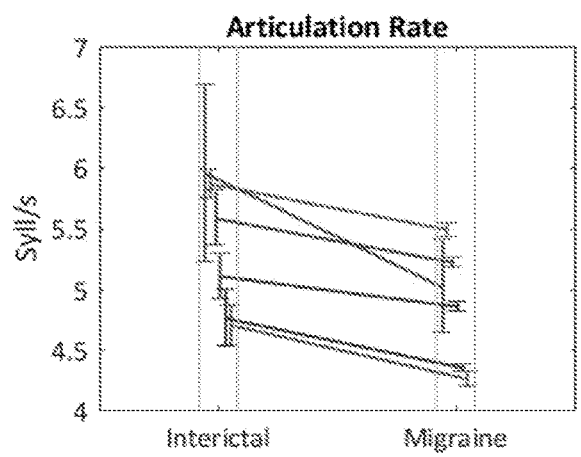
Figure 6D:
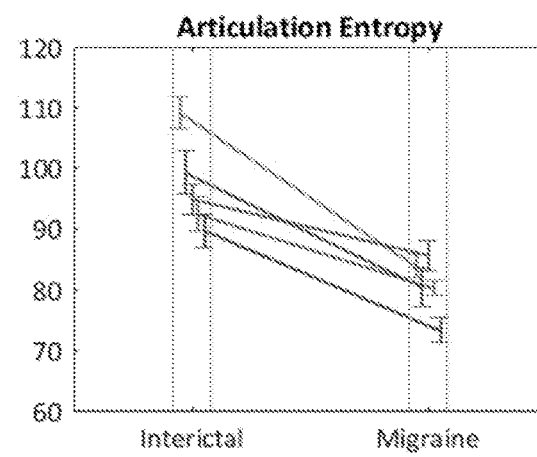
Figure 6E:
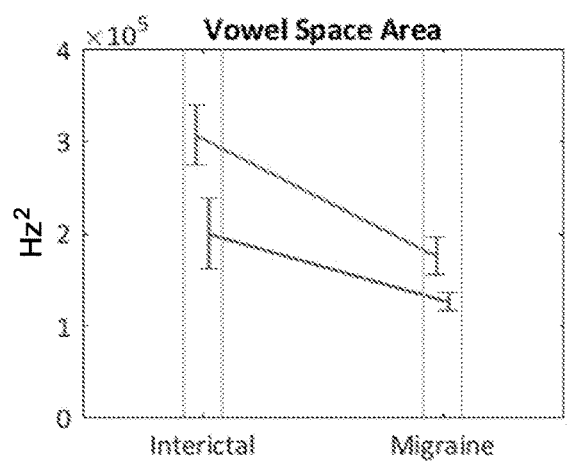
Figure 6F:
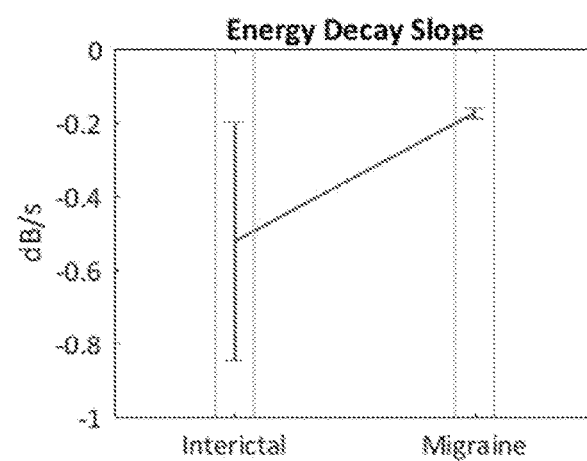
Figure 6G:
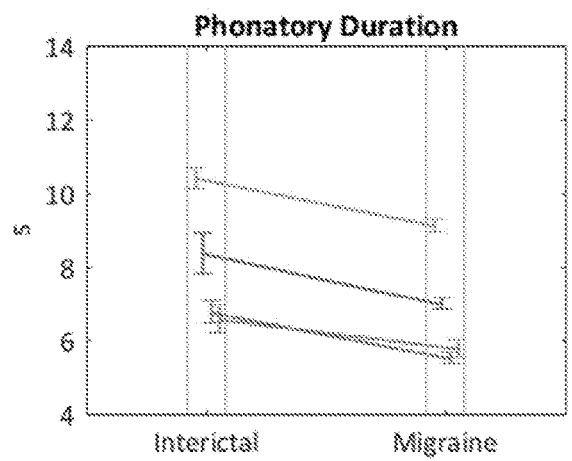
Figure 6H:
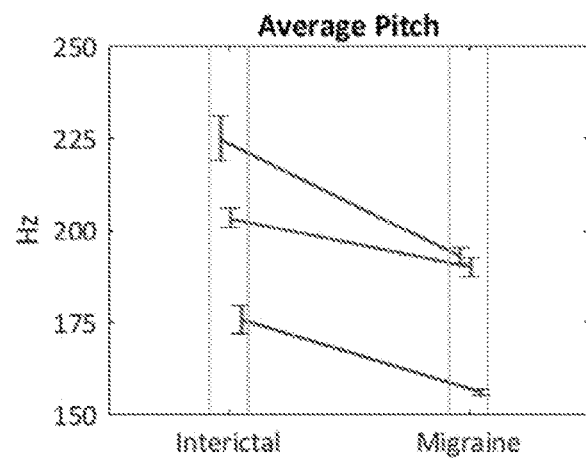
Figure 8A:
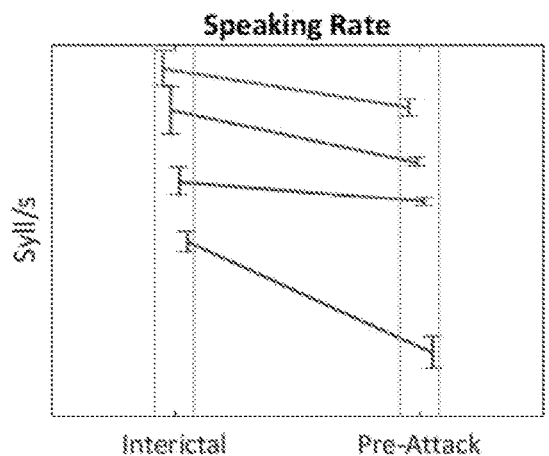
FIGS. 8A-8G are line charts providing mean and standard error plots for seven speech features (speaking rate, articulation rate, articulation entropy, vowel space area, energy decay slope, phonatory duration, and average pitch) that significantly differed during interictal versus migraine pre-attack phases, with each line representing a single individual participant with migraine.
Figure 8B:
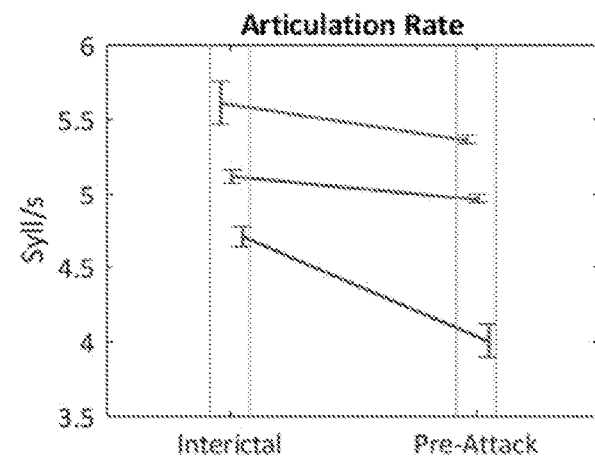
Figure 8C:
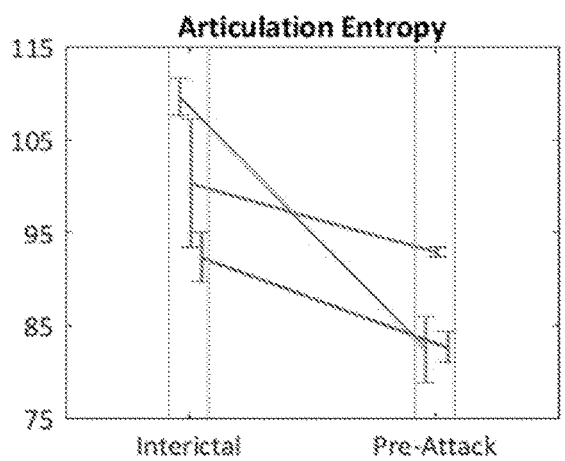
Figure 8D:
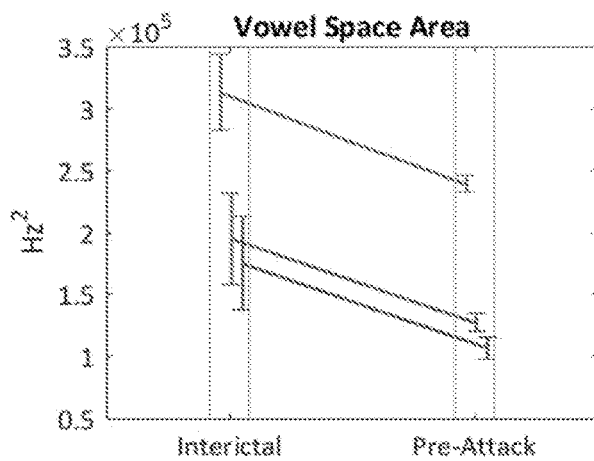
Figure 8E:
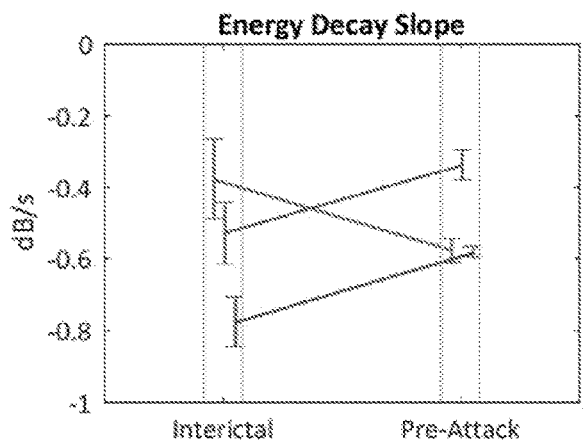
Figure 8F:
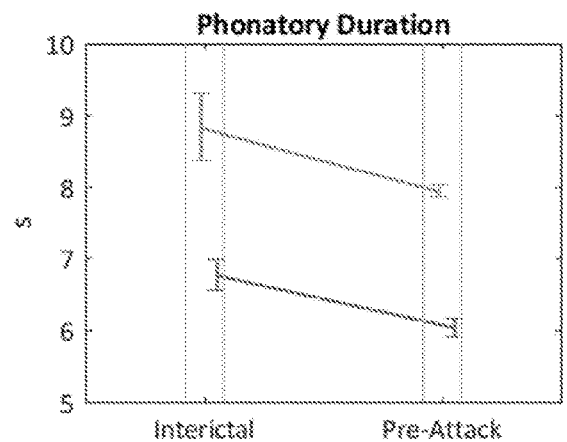
Figure 8G:
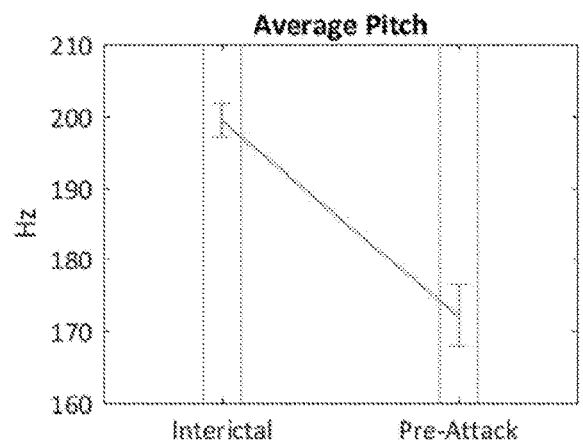

In certain aspects, the present disclosure relates to a migraine identification device, a migraine identification system, methods of operating a migraine identification device, methods of identifying migraine and assessing efficacy of therapeutic interventions (e.g., pharmaceuticals) in treating migraine, and a non-transitory computer readable medium.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Speech analysis devices and methods for identifying migraine attacks are provided. Migraine sufferers can experience changes in speech patterns both during a migraine attack and in a pre-attack phase (e.g., a time period before the migraine attack can be recognized by the migraine sufferer). Embodiments identify or predict migraine attacks during the pre-attack phase and/or the attack phase (such as early stages of a migraine attack) by comparing speech features from one or more speech samples provided by a user against baseline data. The speech features are indicative and/or predictive of migraine onset, and can be personalized to a user and/or based on normative data.

In some examples, a speech sample is elicited from a user (e.g., periodically or on demand), and a multi-dimensional statistical signature of the user's current speech production abilities is generated for the speech sample (e.g., based on the speech features). The multi-dimensional statistical signature is compared against one or more baseline statistical signatures of speech production ability. The baseline statistical signatures can be derived or obtained from the user in some examples, and can alternatively or additionally be based on normative data from a database (e.g., other users). This approach provides a tool to enable migraine sufferers to take therapeutic measures before a full-blown migraine occurs. Such treatment measures may avoid the migraine attack or reduce its severity, thereby reducing any disability associated with a migraine attack. In some cases, information derived from the speech sample(s) is also combined with additional data collected by sensors or input by the user, such as exposure to potential migraine triggers and self-reported symptoms that may occur during a premonitory phase of migraine. Such additional data may be part of the multi-dimensional statistical signature or may be used in analyzing the multi-dimensional statistical signature.

Before discussing specifics of a migraine identification system and method, an experimental study to compare objective features of speech during the pre-attack and attack phases of a migraine episode and during interictal periods (e.g., periods between migraine attacks) will be described. The study was a prospective, longitudinal, observational study of adults with episodic migraine and healthy non-migraine controls. Baseline characteristics were collected during a single in-office visit. Participants then provided speech samples three times per day using a speech elicitation tool included within a mobile application. Participants with migraine also maintained a daily headache diary using the same mobile application. Six complementary speech features that capture articulation and prosody were extracted from participant speech samples. Independent sample t-tests were used to find group differences in speech features between controls, the pre-attack phase (e.g., 0-12 hours prior to an individual recognizing the start of a migraine attack), the migraine attack phase, and the interictal period (e.g., at least 48 hours since end of last migraine and prior to next migraine).

The aim of this study was to determine if objectively measurable changes in speech occur during the twelve hours prior to an individual recognizing that they are having a migraine attack (referred to as the "pre-attack" phase hereafter) and during the migraine attack compared to the interictal period.

Data from fifteen individuals with migraine and fifteen age and gender-matched healthy controls were collected. In total, 56,767 speech samples were collected, including 13,665 speech samples from healthy controls and 43,102 speech samples from individuals with migraine. Amongst those with migraine, 11,253 speech samples were collected during the interictal phase, 2,475 speech samples were collected during the pre-attack phase, and 2,079 speech samples were collected during migraine attacks. Significant group-level differences in speech features were identified between those with migraine and healthy controls and within the migraine group during the pre-attack vs. attack vs. interictal periods (all having $p<0.05$). Most consistently, speech changes occurred in speaking rate, articulation rate and precision, and phonatory duration. Nine of fifteen individuals with migraine showed a change in at least one speech feature when comparing the migraine attack vs. interictal phase and the pre-attack vs. interictal phases.

Methods used in the study will now be described.

Research Participants

This Mayo Clinic Institutional Review Board (IRB)-approved study was conducted between January and December of a single calendar year. All participants completed an informed consent process. Participants were required to be eighteen years of age or older, native English speakers, and willing to record speech samples three times per day. Potential participants were excluded if they had a known speech or language disorder, if they drank more than two alcoholic beverages per week, if they used illicit drugs, and if they used prescription drugs that could impact speech and language patterns (e.g., topiramate). Healthy controls had no personal history of migraine. Participants with migraine reported having between four and ten migraine attacks and fewer than fifteen headache days per month on average over the three months prior to enrollment. Individuals who had migraine with aura were excluded. Migraine diagnoses were made according to the diagnostic criteria of the International Classification of Headache Disorders 3 beta. Healthy controls were age and sex-matched to the participants with migraine.

Baseline Study Visit

During a single baseline study visit, data was collected on participant demographics, headache and migraine attack frequency, migraine attack features, and premonitory symptoms. Participants reported whether they had premonitory symptoms and if so, selected their symptoms from a list and reported how often their migraine attacks were preceded by premonitory symptoms. Participants were provided with a tablet that contained a headache diary mobile application with integrated speech elicitation tasks. Participants were trained on how to use the application and practiced doing so under the supervision of the research team.

FIG. 1 is a table providing reported values for migraine characteristics, including headache frequency, migraine attack frequency, percentage of patients reporting premonitory symptoms, and percentage of reported migraine attacks with premonitory symptoms. The baseline report values are retrospective self-assessments obtained during the baseline study visit, and per diary values are derived from prospectively maintained daily headache diaries. Mean and standard deviation (SD) values are provided for the baseline report values and per diary values.

FIG. 2 is a table providing premonitory symptoms reported at baseline and premonitory symptoms reported in diary (expressed in percentage of patients with a given symptom). During the baseline study visit, participants were asked if they experienced any premonitory symptoms and to select premonitory symptoms that they had ever experienced from a written list. The list included light sensitivity, neck stiffness, generalized feeling of being unwell, fatigue/tiredness, sound sensitivity, mood change, odor sensitivity/distortions, dizzy/lightheaded, temperature changes (e.g., chills, sweats), yawning, muscle pain, vision change, nausea, problems speaking, facial flushing/pale face, food cravings, gastrointestinal (GI) symptoms, and increased urination. In the headache diary, participants were asked if they experienced any of the premonitory symptoms each time they recorded an episode of headache. In this table, a patient was considered to experience a premonitory symptom if they recorded having that symptom with one or more migraine attacks.

Follow-Up Telephone Calls

Participants were contacted by telephone each two weeks to determine if there were any time periods during which their speech may have been impacted by factors other than migraine (e.g., laryngitis). When such conditions were present, speech samples collected on those dates were excluded from analysis.

Headache Diary

Participants with migraine were asked to maintain a daily electronic headache diary for a minimum of three months. If a participant did not experience at least twenty migraine attacks by the conclusion of three months, they were asked to continue their participation until they had twenty migraine attacks, up to a maximum of six months of participation. Each day, participants were asked to input whether they had a headache that day. When they experienced a headache, participants provided information on start and stop times, headache severity, location, quality, and presence of light sensitivity, sound sensitivity, nausea, vomiting, and worsening of pain with routine physical activity. Participants indicated all premonitory symptoms that they experienced by choosing from a list of potential symptoms (the potential symptoms listed in FIG. 2).

Speech Sampling, Processing and Analyses

Healthy controls were asked to provide speech samples three times per day, equally dispersed throughout waking hours, for one month. Participants with migraine also provided speech samples three times per day and were asked to provide an additional speech sample during migraine attacks. Participants with migraine recorded speech samples for at least three months, up to six months or until they had recorded twenty migraine attacks in their headache diary.

Speech samples were collected via the same mobile application that contained the headache diary. While recording a speech sample, participants were instructed to hold the device twelve inches from their mouth and speak in a normal conversational manner. The speech paradigm consisted of reading and reciting five sentences, enunciating four vowel sounds for as long as possible, and repeating the word "buttercup" as many times as possible in one breath. The recorded samples were automatically uploaded to a secured site.

Speech Analytics

For those with migraine, diary information was used to identify which speech samples were collected during migraine attacks. Speech samples were categorized to the pre-attack phase if they occurred 0-12 hours before a reported migraine attack onset and interictal if they occurred 48 hours before the start and 48 hours after the end of a migraine attack.

Six complementary feature sets that represent physical characteristics of speech were extracted from participant speech recordings, including the following items 1-6 described below.

1. Articulation Entropy—a proxy measure of articulatory precision, or the accuracy with which articulators (e.g. tongue, lips, palate) achieve their targets. Articulation entropy accomplishes this measurement by estimating the number of distinct sounds a speaker is capable of producing.
2. Rate Features—Speaking Rate, Pause Rate, Articulation Rate—speaking rate measures the rate at which a speaker enunciates syllables in a sentence, including time spent pausing between words. Similarly, articulation rate measures the rate of syllable enunciation after removing pauses from the speech. Removing pauses provides an estimate for the speed at which the articulators are moving. Lastly, the pause rate measures the percentage of a sentence that a speaker spends pausing in between words.
3. Vowel Space Area—the area of the quadrilateral in vowel space formed by the first and second formants of the four English corner vowels. Because formants (resonant peaks in the frequency spectrum of speech) relate to the kinematics of speech production (e.g., tongue position, mouth cavity size and shape), vowel space area can be used to measure changes in articulatory control.
4. Loudness Decay Slope—during a sustained phonation, the rate at which a speaker's volume decreases over time was measured. A large loudness decay slope can be an indicator of fatigue.
5. Phonatory Duration—during a sustained phonation, the length of time a speaker can produce a vowel sound (phonation) before stopping to take a breath was measured.
6. Average Pitch—the fundamental frequency of a speaker's voice averaged across the duration of five sentences.

Data Analyses

Descriptive statistics are provided for participant demographics, baseline headache characteristics and daily headache diary data. Independent sample t-tests were used to identify group differences in the speech features between healthy controls, the pre-attack phase, the interictal phase, and during migraine attacks. Paired t-tests were also used to compare speech features in the interictal phase to the migraine and pre-attack phases for individual migraine sufferers. For all tests, feature differences were considered significant with $p<0.05$.

Experimental Results

The fifteen healthy control and fifteen migraine participants were well balanced for age and sex. Both the healthy control and migraine group contained thirteen female and two male participants. The average participant age was 44.5+/−13 years in the migraine group and 43.1+/−14 years in the control group. 1426 days of headache diary data, including 424 headache days of which 323 days met criteria for migraine/probable migraine, were collected from the fifteen migraine participants.

Between the individuals with migraine and the fifteen healthy controls, 56,767 speech samples were collected (11 samples per recording session), including 13,665 speech samples from healthy controls and 43,102 speech samples from individuals with migraine. Amongst those with migraine, 11,253 speech samples were collected during the interictal phase, 2,475 speech samples were collected during the pre-attack phase, and 2,079 speech samples were collected during a migraine attack.

FIG. 1 includes headache and migraine frequency reported according to retrospective recall at the baseline study visit and prospectively recorded in headache diaries. At baseline, average headache frequency was reported as 9.3 days per month and average migraine attack frequency was 6.2 per month. Per headache diaries, average headache frequency was 8.9 days per month and average migraine attack frequency was 6.8 per month.

Information about premonitory symptoms is found in FIGS. 1 and 2. At baseline, all individuals with migraine reported having premonitory symptoms with at least some of their attacks. On average, they reported that 90% of their migraine attacks were preceded by premonitory symptoms and that when they noted symptoms thought to be premonitory in nature, 86.7% of the time a migraine attack followed. According to headache diaries, 72.1% of migraine attacks were preceded by premonitory symptoms. At baseline, the most commonly reported premonitory symptoms based upon participant recall included (in descending order of frequency): light sensitivity, neck stiffness, fatigue/tiredness, generalized feeling of being unwell, and sound sensitivity. Problems speaking were reported by 20% of the individuals with migraine. According to prospective headache diaries, the most commonly reported premonitory symptoms included (in descending order of frequency): generalized feeling of being unwell, fatigue/tiredness, neck stiffness, mood changes, and light sensitivity. Problems speaking were reported by 27% of participants.

Speech Features

FIG. 3 is a table providing speech features for healthy controls and participants with migraine during interictal, pre-attack, and migraine attack phases. FIG. 3 contains average values and standard deviations of speech feature sets, including speaking rate (in syllables per second (syllables/s or syll/s)), pause rate (as a percentage of recording length), articulation rate (in syllables/s), articulation entropy, vowel space area (in square hertz ($Hz^2$)), energy decay slop (in decibels per second (dB/s)), phonatory duration (in seconds (s)), and average pitch (in hertz (Hz)).

Comparing Individuals with Migraine to Healthy Controls

FIG. 4 is a table providing p-values for comparison of eight speech features (speaking rate, pause rate, articulation rate, articulation entropy, vowel space area, energy decay slope, phonatory duration, and average pitch), including comparisons within a migraine group as well as comparisons of migraine versus healthy control groups. Speech patterns of those with migraine were compared against the group of age-and-gender-matched healthy controls.

There were several group-level differences that indicated a loss in articulatory precision, a change in speech rhythm, and phonatory fatigue during migraine attacks and during the pre-attack phase compared to healthy controls. In particular, migraine participants exhibited decreased articulation entropy and increased pause rate during migraine attacks and the pre-attack phase compared to healthy controls. In addition, migraine sufferers had significantly lower values of phonatory duration during a migraine attack, pre-attack phase, and interictal phase when compared to healthy controls.

There were also group-level differences between healthy controls and those with migraine in the interictal phase. Healthy controls were shown to have significantly lower speaking and articulation rates compared to migraine sufferers during the interictal period. Additionally, the t-tests revealed significantly lower phonatory duration and increased loudness decay slope in migraine sufferers during interictal periods. These results are shown in FIGS. 3 and 4.

Referring to FIG. 4, as a group, those with migraine had alterations in several speech parameters during their interictal, migraine pre-attack and migraine attack phases compared to healthy controls. Furthermore, there were changes in speech parameters during the migraine pre-attack and migraine attack phases compared to the interictal period.

Comparing Migraine Pre-Attack, Migraine Attack and Interictal Phases

Nine of the fifteen migraine participants showed significant changes in speech patterns between interictal and attack phases. Of these nine patients, eight had significant differences in more than one speech feature.

FIG. 5 is a table providing p-values for eight speech features (speaking rate, pause rate, articulation rate, articulation entropy, vowel space area, energy decay slope, phonatory duration, and average pitch) for migraine attack versus interictal phase for these nine individual participants. FIG. 5 lists the significant p-values of these tests by numbered participant, and FIGS. 6A-6H plot the speech changes between interictal and migraine phases by participant.

FIGS. 6A-6H are eight line charts providing mean and standard error plots for the eight speech features of FIG. 5 that significantly differed during interictal versus migraine attack phases, with each line representing a single individual participant with migraine.

Additionally, nine of the fifteen migraine participants showed significant changes in speech patterns between the interictal and pre-attack phase.

FIG. 7 is a table providing p-values for eight speech features (speaking rate, pause rate, articulation rate, articulation entropy, vowel space area, energy decay slope, phonatory duration, and average pitch) for migraine pre-attack versus interictal phase for these nine individual patients. When comparing the pre-attack and interictal phases, four patients had significant changes in speaking rate, three had significant changes in articulation rate, articulation entropy, energy decay slope, and vowel space area, and two had significant changes to phonatory duration.

FIGS. 8A-8G are line charts providing mean and standard error plots for seven speech features (speaking rate, articulation rate, articulation entropy, vowel space area, energy decay slope, phonatory duration, and average pitch) that significantly differed during interictal versus migraine pre-attack phases, with each line representing a single individual participant with migraine.

Experimental Discussion

The experimental study investigated objective changes in speech that occur prior to and during migraine attacks. The study showed that the majority of participants had changes in speech during the migraine attack compared to their interictal phase. The most common changes were slowing of speaking rate and a decrease in articulatory precision, indicating a measurable decrease in speech motor excursions during a migraine attack. Significant changes in speaking rate and articulatory precision were observed at the group level and within the nine participants who exhibited speech pattern changes. Additionally, significant speech pattern changes were observed during the migraine pre-attack phase in nine of fifteen participants with migraine. The most common speech pattern disruptions during the pre-attack phase were changes in articulatory precision, speaking rate, and articulation rate. Furthermore, there were group-level differences in speaking rate, articulation rate, energy decay slope, and phonatory duration between interictal migraine sufferers and healthy controls. These differences can be explained by idiosyncratic differences in speaking style between the two groups. Despite the fact that great precaution was taken in matching subjects by gender and age, there can still be differences in speaking style between the two groups. This further motivates the within-subject analysis.

Difficulties with speech and language have been documented during the aura phase of migraine. However, self-reported speech alterations and objectively measured alterations in speech associated with migraine have been inadequately investigated during the non-aura phases of the migraine attack and during the interictal period.

Subjective self-reported changes in speech during pre-monitory and headache phases of a migraine attack have been reported within a few studies. Patient reported speech difficulties were reported during 9% of recorded migraine premonitory phases and 19.9% of recorded migraine headache attacks in a previous electronic headache diary study of 97 individuals. Furthermore, identification of speech difficulties during the premonitory phase was strongly associated with an oncoming migraine attack. In a prospective study of 100 episodic migraine patients, 17% reported speech difficulties as a premonitory symptom. In the study described herein, 20% of participants retrospectively recalled having speech problems during the premonitory phase and 27% reported such symptoms prospectively, frequencies that are more-or-less consistent with those reported in prior publications.

The frequency of objectively measured changes in speech during migraine attacks and in the pre-attack phase was previously unknown. In contrast to the relatively low frequency of self-reported speech changes reported in the literature and by the subjects in the study detailed above, 60% of participants in this study had significant changes in speech during migraine attacks as well as within the twelve hours preceding self-recognition of a migraine attack starting. According to this work, changes in speech are a common symptom during a migraine attack, perhaps nearly as common as nausea, as common as unilateral headache (as opposed to bilateral), and more common than vomiting, which are key features for defining a migraine attack.

An extension of the preceding work includes joint analysis of speech production and language processing as early indicators of migraine. One previous published study analyzed the language processing abilities in a group of migraine sufferers who had speech disturbances with migraine attacks (reported by the patient or their relative) and in a matched group who did not report speech disturbances. That study showed that the group reporting speech disturbances had increased language processing reaction times when tested during the interictal phase.

In conclusion, migraine is associated with alterations in speech. Alterations in speech may be present in individuals with migraine between migraine attacks compared to healthy controls and further speech changes occur during the migraine pre-attack and migraine attack phases compared to the interictal period. The relative ease with which speech can be collected using mobile technology makes identification of pre-attack changes in speech an appealing objective harbinger for an oncoming attack.

Having described the foregoing experimental study, a migraine identification system, migraine identification device, and associated methods will now be described.

Figure 9:
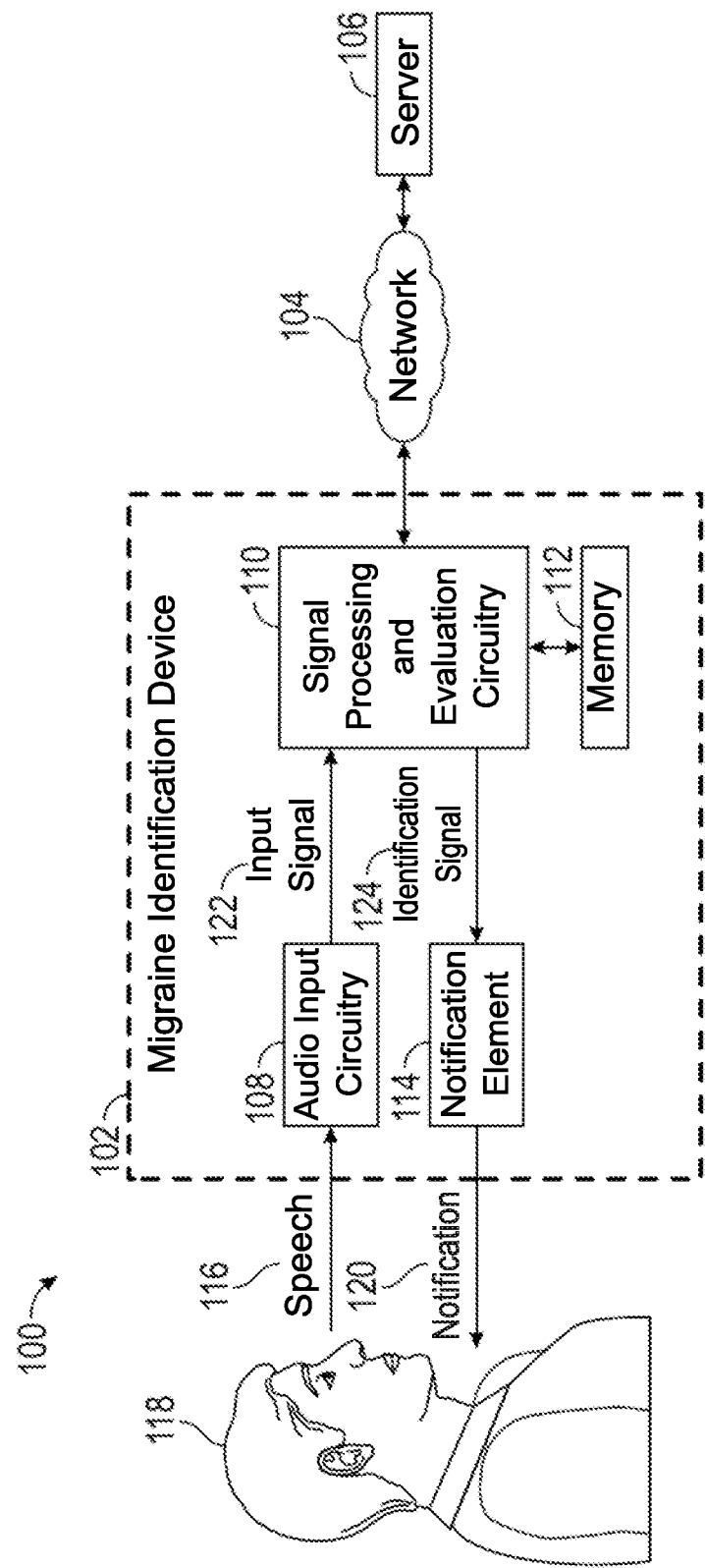
FIG. 9 is a schematic diagram depicting a migraine identification system including a migraine identification device, a network, and a server; the migraine identification device including audio input circuitry, signal processing circuitry, a memory, and a notification element; and the signal processing circuitry being configured to provide a migraine identification signal based on characteristics of speech provided by a user.

FIG. 9 is a diagram of a migraine identification system 100 comprising a migraine identification device 102, a network 104, and a server 106. The migraine identification device 102 comprises audio input circuitry 108, signal processing circuitry 110, memory 112, and at least one notification element 114. In certain embodiments, the signal processing circuitry 110 may include, but not necessarily be limited to, audio processing circuitry. The audio input circuitry 108, notification element(s) 114, and memory 112 may be coupled with the signal processing circuitry 110 via wired connections, wireless connections, or a combination thereof. The migraine identification device 102 may further comprise a smartphone, a smartwatch, a wearable sensor, a computing device, a headset, a headband, or combinations thereof. The migraine identification device 102 may be configured to receive speech 116 from a user 118 and provide a notification 120 to the user 118 based on processing the speech 116 to assess whether a migraine attack is or is not identified or expected.

The audio input circuitry 108 may comprise at least one microphone. In certain embodiments, the audio input circuitry 108 may comprise a bone conduction microphone, a near field air conduction microphone array, or a combination thereof. The audio input circuitry 108 may be configured to provide an input signal 122 that is indicative of the speech 116 provided by the user 118 to the signal processing circuitry 110. The input signal 122 may be formatted as a digital signal, an analog signal, or a combination thereof. In certain embodiments, the audio input circuitry 108 may provide the input signal 122 to the signal processing circuitry 110 over a personal area network (PAN). The PAN may comprise Universal Serial Bus (USB), IEEE 1394 (FireWire) Infrared Data Association (IrDA), Bluetooth, ultra-wideband (UWB), Wi-Fi Direct, or a combination thereof. The audio input circuitry 108 may further comprise at least one analog-to-digital converter (ADC) to provide the input signal 122 in digital format.

The signal processing circuitry 110 may comprise a communication interface (not shown) coupled with the network 104 and a processor (e.g., an electrically operated microprocessor (not shown) configured to execute a pre-defined and/or a user-defined machine readable instruction set, such as may be embodied in computer software) configured to receive the input signal 122. The communication interface may comprise circuitry for coupling to the PAN, a local area network (LAN), a wide area network (WAN), or a combination thereof. The processor may be configured to receive instructions (e.g., software, which may be periodically updated) for extracting a multi-dimensional statistical signature of speech production abilities of the user 118 that spans multiple perceptual dimensions. Such perceptual dimensions may include any one or more of (A) articulation (providing measures of articulatory precision and articulator control); (B) prosodic variability (providing measures of intonational variation over time); (C) phonation changes (providing measures related to pitch and voicing); and (D) rate and rate variation (providing measures related to speaking rate and how it varies).

Extracting the multi-dimensional statistical signature of speech production abilities of the user 118 can include measuring one or more of the speech features described above (e.g., with respect to FIGS. 4-8B) which may be indicative of migraine onset. For example, the speech features may include one or more of speaking rate, articulation rate, articulation entropy, vowel space area, energy decay slope, phonatory duration, and average pitch.

Machine learning algorithms based on these acoustic measures may be used to identify and/or predict an oncoming migraine attack. In certain embodiments, machine learning algorithms may use clusters of acoustic measures derived from a speech input signal and produce a binary migraine identification signal (e.g., migraine attack is occurring or expected/no migraine attack is occurring or expected). In certain embodiments, the migraine identification signal is non-binary, such as estimating a chance of migraine occurrence (e.g., to notify a user that "you have an 80% chance of developing a migraine today."). In certain embodiments, an instantaneous multi-dimensional statistical signature may be normalized and/or compared against one or more baseline statistical signatures of speech production ability derived or obtained from the same subject (optionally augmented with statistical signatures and/or other information obtained from different subjects) to produce a migraine identification signal.

In certain embodiments, such machine learning algorithms (or other signal processing approaches) may compare the multi-dimensional statistical signature against one or more baseline statistical signatures of speech production ability by comparing each of several speech feature (e.g., speaking rate, articulation rate, articulation entropy, vowel space area, energy decay slope, phonatory duration, and average pitch) to a corresponding baseline speech feature of the one or more baseline statistical signatures of speech production ability. In certain embodiments, the machine learning algorithms may also take into account additional data, such as sensor data (e.g., from an accelerometer or environmental sensor), a time of day, an ambient light level, and/or a device usage pattern of the user.

In some cases, additional data can include input by the user, such as exposure to potential migraine triggers and self-reported symptoms that may occur during the premonitory phase of migraine. Such additional data may be part of the multi-dimensional statistical signature or may be used in analyzing the multi-dimensional statistical signature. For example, the additional data may be used to select or adjusting the baseline statistical signatures of speech used in producing the migraine identification signal.

In certain embodiments, the processor may comprise an ADC to convert the input signal 122 to digital format. In other embodiments, the processor may be configured to receive the input signal 122 from the PAN via the communication interface. The processor may further comprise level detect circuitry, adaptive filter circuitry, voice recognition circuitry, or a combination thereof. The processor may be further configured to process the input signal 122 using a multi-dimensional statistical signature and/or clusters of acoustic measures derived from a speech input signal and produce a binary migraine identification signal, and provide a migraine identification signal 124 to the notification element 114. The migraine identification signal 124 may be in a digital format, an analog format, or a combination thereof. In certain embodiments, the migraine identification signal 124 may comprise one or more of an audible signal, a visual signal, a vibratory signal, or another user-perceptible signal. In certain embodiments, the processor may additionally or alternatively provide the migraine identification signal 124 over the network 104 via a communication interface.

The processor may be further configured to generate a record indicative of the migraine identification signal 124. The record may comprise a sample identifier and/or an audio segment indicative of the speech 116 provided by the user 118. In certain embodiments, the user 118 may be prompted to provide current symptoms or other information about their current wellbeing to the migraine identification device 102. Such information may be included in the record, and may further be used to aid in identification or prediction of a current and future migraine attacks.

The record may further comprise a location identifier, a time stamp, a physiological sensor signal (e.g., heart rate, blood pressure, temperature, or the like), or a combination thereof being correlated to and/or contemporaneous with the migraine identification signal 124. The location identifier may comprise a Global Positioning System (GPS) coordinate, a street address, a contact name, a point of interest, or a combination thereof. In certain embodiments, a contact name may be derived from the GPS coordinate and a contact list associated with the user 118. The point of interest may be derived from the GPS coordinate and a database including a plurality of points of interest. In certain embodiments, the location identifier may be a filtered location for maintaining the privacy of the user 118. For example, the filtered location may be "user's home", "contact's home", "vehicle in transit", "restaurant", or "user's work". In certain embodiments, the record may include a location type, wherein the location identifier is formatted according to the location type.

The processor may be further configured to store the record in the memory 112. The memory 112 may be a non-volatile memory, a volatile memory, or a combination thereof. The memory 112 may be wired to the signal processing circuitry 110 using an address/data bus. In certain embodiments, the memory 112 may be portable memory coupled with the processor.

In certain embodiments, the processor may be further configured to send the record to the network 104, wherein the network 104 sends the record to the server 106. In certain embodiments, the processor may be further configured to append to the record a device identifier, a user identifier, or a combination thereof. The device identifier may be unique to the migraine identification device 102. The user identifier may be unique to the user 118. The device identifier and the user identifier may be useful to a medical treatment professional and/or researcher, wherein the user 118 may be a patient of the medical treatment professional.

The network 104 may comprise a PAN, a LAN, a WAN, or a combination thereof. The PAN may comprise USB, IEEE 1394 (FireWire) IrDA, Bluetooth, UWB, Wi-Fi Direct, or a combination thereof. The LAN may include Ethernet, 802.11 WLAN, or a combination thereof. The network 104 may also include the Internet.

The server 106 may comprise a personal computer (PC), a local server connected to the LAN, a remote server connected to the WAN, or a combination thereof. In certain embodiments, the server 106 may be a software-based virtualized server running on a plurality of servers.

In certain embodiments, at least some signal processing tasks may be performed via one or more remote devices (e.g., the server 106) over the network 104 instead of within a migraine identification device 102 that houses the audio input circuitry 108.

In certain embodiments, migraine identification or prediction based on audio input signals may be augmented with signals indicative of physiological state and/or activity level of a user (e.g., heart rate, blood pressure, temperature, etc.). For example, audio input signals may be affected by activity level and/or physiological state of a user. In certain embodiments, a multi-dimensional statistical signature of speech production abilities obtained from a user may be normalized based on physiological state and/or activity level of the user before comparison is made against one or more baseline statistical signatures of speech production ability derived or obtained from the user, to avoid false positive or false negative migraine identification signals. In certain embodiments, the one or more baseline statistical signatures of speech production ability are at least partially based on normative acoustic data from a database. For example, the baseline statistical signature(s) may be produced by a machine learning algorithm trained with past data for other users.

In certain embodiments, a migraine identification device 102 may be embodied in a mobile application configured to run on a mobile computing device (e.g., smartphone, smartwatch) or other computing device. With a mobile application, speech samples can be collected remotely from patients and analyzed without requiring patients to visit a clinic. A user 118 may be periodically queried (e.g., two, three, four, five, or more times per day) to provide a speech sample. For example, the notification element 114 may be used to prompt the user 118 to provide speech 116 from which the input signal 122 is derived, such as through a display message or an audio alert. The notification element 114 may further provide instructions to the user 118 for providing the speech 116 (e.g., displaying a passage for the user 118 to read). In certain embodiments, the notification element 114 may request current symptoms or other information about the current wellbeing of the user 118 to provide additional data for analyzing the speech 116.

In addition, whenever a user feels a migraine episode coming on, the user may open the application and provide a speech sample (e.g., spontaneously provide a speech sample). In certain embodiments, data collection may take no longer than 2-3 minutes as users are asked to read a carefully designed passage (e.g., paragraph) that evaluates the user's ability to produce all of the phonemes in the user's native language (e.g., English). Restated, a user may be provided with one or more speaking prompts, wherein such prompts may be tailored to the type of speech (data) that clinicians are interested in capturing. Examples of speaking tasks that may be prompted by a user include unscripted speech, reciting scripted sentences, and/or holding a single tone as long as possible (phonating). In certain embodiments, data collection may take additional time. In certain embodiments, the migraine identification device may passively monitor the user's speech, and if a change in speech patterns is detected initiate an analysis to generate the instantaneous multi-dimensional statistical signature of speech production abilities of the user.

In certain embodiments, a notification element (e.g., notification element 114 in FIG. 3) may include a display (e.g., LCD display) that displays text and prompts the user to read the text. Each time the user provides a new sample using the mobile application, a multi-dimensional statistical signature of the user's speech production abilities may be automatically extracted. One or more machine-learning algorithms based on these acoustic measures may be implemented to aid in identifying or predicting an oncoming migraine attack.

In certain embodiments, a migraine identification signal 124 provided to the notification element 114 can instruct the user 118 to take action to relieve migraine symptoms. Such actions may include adjusting the environment (e.g., informed by sensor data received by the mobile application), reducing work or other stress loads, taking medicine or other treatments, and so on. In some examples, the instructions may be customized to the user 118 based on previously successful interventions.

In certain embodiments, a user may download a mobile application to a personal computing device (e.g., smartphone), optionally sign in to the application, and follow the prompts on a display screen. Once recording has finished, the audio data may be automatically uploaded to a secure server (e.g., a cloud server or a traditional server) where the signal processing and machine learning algorithms operate on the recordings.

Figure 10:
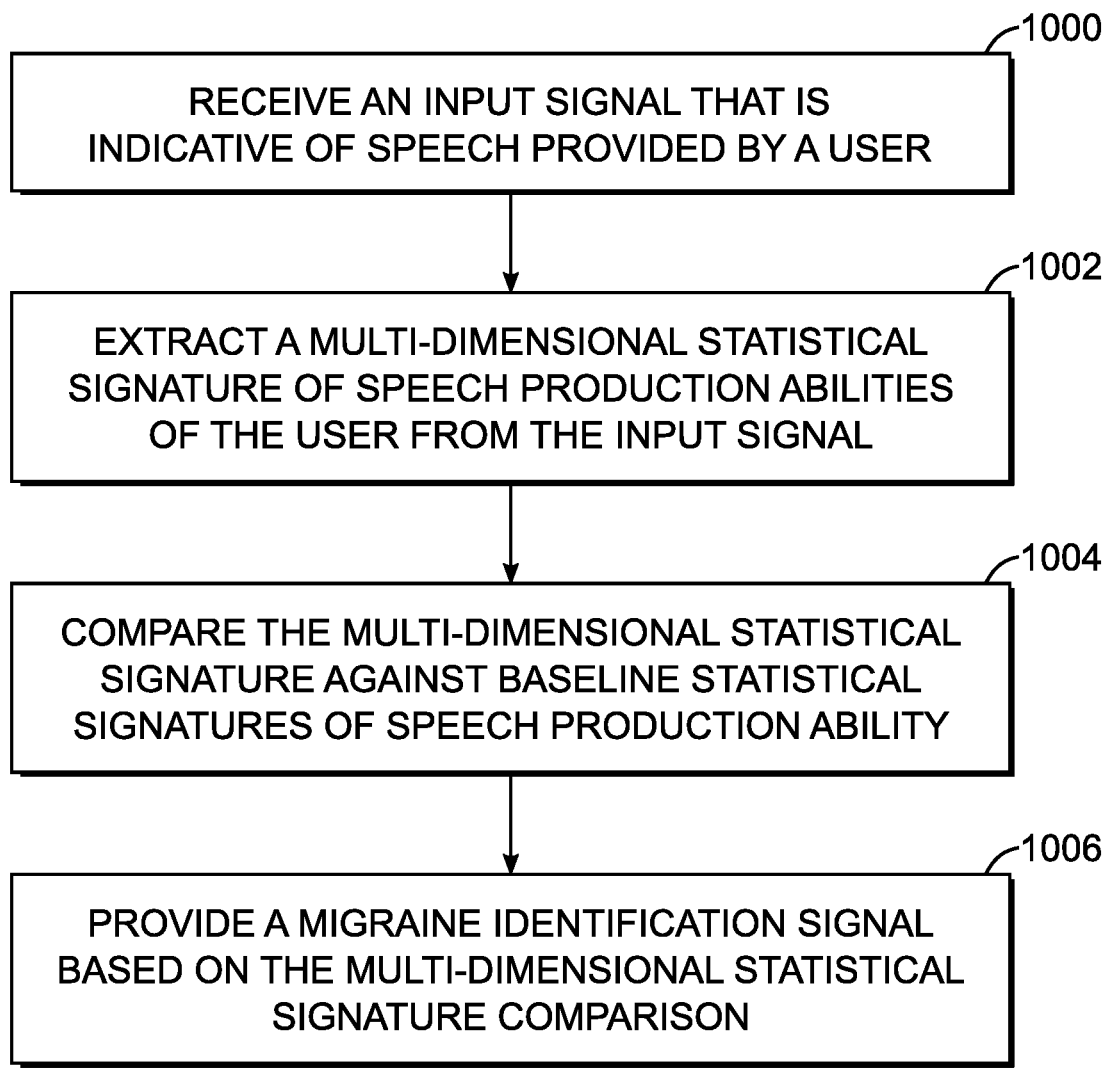
FIG. 10 is a flow diagram illustrating a process for identifying a migraine according to one embodiment.

FIG. 10 is a flow diagram illustrating a process for identifying a migraine. The process may be performed by one or more components of the migraine identification system 100 of FIG. 9, such as the migraine identification device 102 or the server 106. The process begins at operation 1000, with receiving an input signal that is indicative of speech provided by a user. The process continues at operation 1002, with extracting a multi-dimensional statistical signature of speech production abilities of the user from the input signal. The process continues at operation 1004, with comparing the multi-dimensional statistical signature against one or more baseline statistical signatures of speech production ability. The process continues at operation 1006, with providing a migraine identification signal based on the multi-dimensional statistical signature comparison.

Although the operations of FIG. 10 are illustrated in a series, this is for illustrative purposes and the operations are not necessarily order dependent. Some operations may be performed in a different order than that presented. Further, processes within the scope of this disclosure may include fewer or more steps than those illustrated in FIG. 10.

The disclosed approach enables new methods for objective identification and/or prediction of migraine attacks and rapid therapeutic intervention. In certain embodiments, an application running in the background of a mobile phone may passively detect subtle changes in the speech patterns of a migraine sufferer during phone calls, by periodically generating a multi-dimensional statistical signature of a user's speech production abilities and comparing the signature against one or more baseline signatures. When changes in a user's speech production abilities consistent with migraine onset are detected, the phone may notify the user and instruct the user to take appropriate action (e.g., adjusting activity and/or taking medication).

In certain embodiments, the periodic generation of multi-dimensional statistical signatures of a user's speech production abilities for a user undergoing a pharmaceutical treatment regimen for treating migraine may be used to assess efficacy of the treatment regimen.

Those skilled in the art will recognize improvements and modifications to the preferred embodiments of the present disclosure. All such improvements and modifications are considered within the scope of the concepts disclosed herein and the claims that follow.

What is claimed is:
1. A migraine identification device comprising:
audio input circuitry configured to provide an input signal that is indicative of speech provided by a user;
signal processing circuitry including a processor configured to:

receive the input signal, the input signal including one or more speech samples representing speech patterns; and process the input signal to:
- generate an instantaneous multidimensional statistical signature of speech production abilities of the user, and
- compare the multi-dimensional statistical signature against one or more baseline statistical signatures of speech production ability derived or obtained from the user to assess changes in the speech patterns associated with a migraine; and
- provide a migraine identification signal based on the multi-dimensional statistical signature comparison; and a notification element coupled to the signal processing circuitry, the notification element configured to receive the migraine identification signal and provide at least one notification signal to the user.

2. The migraine identification device of claim 1, wherein the multi-dimensional statistical signature spans one or more of the following perceptual dimensions: articulation, prosodic variability, phonation changes, rate, and rate variation.

3. The migraine identification device of claim 1, wherein the signal processing circuitry is configured to process the input signal by measuring speech features represented in the input signal, the speech features comprising one or more of speaking rate, articulation rate, articulation entropy, vowel space area, energy decay slope, phonatory duration, and average pitch.

4. The migraine identification device of claim 3, wherein the signal processing circuitry is configured to compare the multi-dimensional statistical signature against the one or more baseline statistical signatures of speech production ability by comparing each speech feature to a corresponding baseline speech feature of the one or more baseline statistical signatures of speech production ability.

5. The migraine identification device of claim 1, wherein the signal processing circuitry is configured to process the input signal utilizing the input signal and additional data comprising one or more of sensor data, a time of day, an ambient light level, a device usage pattern of the user, or a user input.

6. The migraine identification device of claim 5, wherein the signal processing circuitry is configured to process the input signal by selecting or adjusting the one or more baseline statistical signatures of speech production ability based on the additional data.

7. The migraine identification device of claim 5, wherein the user input comprises at least one of information regarding exposure to potential migraine triggers or a self-reported premonitory migraine symptom.

8. The migraine identification device of claim 1, wherein the migraine identification device is a mobile computing device operating a migraine identification application.

9. The migraine identification device of claim 8, wherein the migraine identification application queries the user periodically to provide a speech sample from which the input signal is derived.

10. The migraine identification device of claim 8, wherein the migraine identification application facilitates the user spontaneously providing a speech sample from which the input signal is derived.

11. The migraine identification device of claim 8, wherein the migraine identification application passively detects changes in speech patterns of the user and initiates generation of the instantaneous multi-dimensional statistical signature of speech production abilities of the user.

12. The migraine identification device of claim 1, wherein the notification element comprises a display.

13. The migraine identification device of claim 12, wherein the signal processing circuitry is further configured to cause the display to prompt the user to provide a speech sample from which the input signal is derived.

14. The migraine identification device of claim 12, wherein the at least one notification signal comprises a display notification instructing the user to take action to relieve migraine symptoms.

15. A method for identifying a migraine, the method comprising:
- receiving an input signal including a speech pattern that is indicative of speech provided by a user; extracting a multi-dimensional statistical signature of speech production abilities of the user from the input signal;
- comparing the multi-dimensional statistical signature against one or more statistical signatures of speech production ability to assess a change in the speech pattern; and
- providing a migraine identification signal based on the multi-dimensional statistical signature comparison.

16. The method of claim 15, wherein the one or more baseline statistical signatures of speech production ability are derived or obtained from the user.

17. The method of claim 15, wherein the one or more baseline statistical signatures of speech production ability are at least partially based on normative acoustic data from a database.

18. The method of claim 15, wherein the comparing the multi-dimensional statistical signature against the one or more baseline statistical signatures of speech production ability comprises applying a machine learning algorithm to the multi-dimensional statistical signature.

19. The method of claim 18, wherein the machine learning algorithm is trained with past comparisons for other users.

20. The method of claim 15, wherein:
- extracting the multi-dimensional statistical signature of speech production abilities of the user from the input signal comprises measuring speech features across one or more of the following perceptual dimensions: articulation, prosodic variability, phonation changes, rate, and rate variation; and
- comparing the multi-dimensional statistical signature against the one or more baseline statistical signatures of speech production ability comprises comparing each speech feature to a corresponding baseline speech feature of the one or more baseline statistical signatures of speech production ability.

21. A non-transient computer readable medium which, when executed by a computer, causes the computer to:
- receive an input signal including a speech pattern that is indicative of speech provided by a user;
- extract a multi-dimensional statistical signature of speech production abilities of the user from the input signal;
- compare the multi-dimensional statistical signature against one or more baseline statistical signatures of speech production ability to assess a change in the speech pattern; and
- provide a migraine identification signal based on the multi-dimensional statistical signature comparison.

* * * * *